United States Patent
Takebayashi et al.

(10) Patent No.: US 9,648,938 B2
(45) Date of Patent: May 16, 2017

(54) COSMETIC TOOL, RETAINER OF COSMETIC MATERIAL AND METHOD OF MANUFACTURING COSMETIC TOOL

(75) Inventors: Takafumi Takebayashi, Yokohama (JP); Hideaki Fukushi, Yokohama (JP); Miki Yamada, Osaka (JP); Kyouko Fukugaki, Osaka (JP); Miyoko Uemura, Osaka (JP); Kozo Tazaki, Osaka (JP); Tomomi Ayasu, Osaka (JP); Tsukasa Mitsui, Osaka (JP)

(73) Assignees: JNC CORPORATION, Tokyo (JP); SUNSTAR INC., Osaka (JP)

( * ) Notice: Subject to any disclaimer, the term of this patent is extended or adjusted under 35 U.S.C. 154(b) by 0 days.

(21) Appl. No.: 14/345,784

(22) PCT Filed: Sep. 12, 2012

(86) PCT No.: PCT/JP2012/073300
§ 371 (c)(1),
(2), (4) Date: Mar. 19, 2014

(87) PCT Pub. No.: WO2013/042592
PCT Pub. Date: Mar. 28, 2013

(65) Prior Publication Data
US 2014/0224274 A1    Aug. 14, 2014

(30) Foreign Application Priority Data
Sep. 21, 2011 (JP) .................................. 2011-205703

(51) Int. Cl.
A45D 33/24    (2006.01)
A45D 33/00    (2006.01)
(Continued)

(52) U.S. Cl.
CPC ............. *A45D 33/00* (2013.01); *A45D 40/00* (2013.01); *A61K 8/0216* (2013.01); *A61K 8/65* (2013.01);
(Continued)

(58) Field of Classification Search
CPC .... A45D 33/006; A45D 40/22; A45D 13/008; A45D 40/221; A45D 33/00;
(Continued)

(56) References Cited

U.S. PATENT DOCUMENTS 3,332,429 A * 7/1967 Bates ........................... 132/317
3,939,260 A    2/1976 Lafon
(Continued)

FOREIGN PATENT DOCUMENTS

CN    1310603    8/2001
CN    2498089    7/2002
(Continued)

OTHER PUBLICATIONS

Notification of the First Office Action issued Oct. 10, 2015 in corresponding Chinese Application No. 201280045973.6 (with English translation).

(Continued)

*Primary Examiner* — Robyn Doan
(74) *Attorney, Agent, or Firm* — Wenderoth, Lind & Ponack, L.L.P.

(57) ABSTRACT

This application aims at providing a retainer of a cosmetic material and a method of manufacturing a cosmetic tool, which are capable of easily treating the cosmetic material even when decreasing a concentration of skin care ingredients of the cosmetic material produced by freeze-drying. A cosmetic tool (1) includes: a retainer (3) to include an annular frame (2) and a handle (5) for holding the frame (2); and a cosmetic material (4) to be produced by freeze-drying
(Continued)

an aqueous solution of skin care ingredients and fixed in a way that covers an aperture of the frame (2).

8 Claims, 5 Drawing Sheets (51) Int. Cl.
    *A45D 40/00*     (2006.01)
    *A61K 8/65*     (2006.01)
    *A61Q 19/00*     (2006.01)
    *A61K 8/02*     (2006.01)

(52) U.S. Cl.
    CPC ........ *A61Q 19/005* (2013.01); *A45D 40/0087* (2013.01); *A45D 2040/0006* (2013.01); *A61K 2800/84* (2013.01); *A61K 2800/87* (2013.01)

(58) Field of Classification Search
    CPC ........ A45D 40/0087; A45D 2040/0006; A61K 8/19; A61K 8/67; A61K 8/72; A61K 8/65; A61K 8/0216
    USPC .......................................... 132/293, 294, 303
    See application file for complete search history.

(56) References Cited

U.S. PATENT DOCUMENTS

| | | | | |
|---|---|---|---|---|
| 5,326,185 | A | * | 7/1994 | Dornbusch et al. ............ 401/88 |
| 5,681,574 | A | | 10/1997 | Haber et al. |
| 5,904,151 | A | * | 5/1999 | Gueret ......................... 132/293 |
| 6,467,981 | B1 | * | 10/2002 | Gueret ......................... 401/201 |
| 6,544,284 | B1 | | 4/2003 | Ujihara et al. |
| 6,840,694 | B2 | * | 1/2005 | Gueret ......................... 401/266 |
| 6,890,115 | B2 | * | 5/2005 | Le Moing, II .................. 401/82 |
| 7,335,220 | B2 | * | 2/2008 | Khosravi ......... A61B 17/00491 606/213 |
| 8,893,731 | B2 | * | 11/2014 | Pires et al. .................... 132/294 |
| 2010/0031971 | A1 | * | 2/2010 | Ha ........................ A45D 33/006 132/293 |

FOREIGN PATENT DOCUMENTS

| | | |
|---|---|---|
| FR | 2 068 447 | 8/1971 |
| FR | 2 478 997 | 10/1981 |
| JP | 2003-19028 | 1/2003 |
| JP | 2005-263759 | 9/2005 |
| JP | 2006182750 A * | 7/2006 |
| JP | 2007-137875 | 6/2007 |
| JP | 2010-163386 | 7/2010 |
| WO | 2008/131804 | 11/2008 |
| WO | 2010/013656 | 2/2010 |
| WO | WO 2010013656 A1 * | 2/2010 |

OTHER PUBLICATIONS

International Preliminary Report on Patentability and Written Opinion of the International Searching Authority issued Apr. 3, 2014 in International (PCT) Application No. PCT/JP2012/073300.

Supplementary European Search Report issued Jan. 5, 2015 in Application No. EP 12834365.4.

International Search Report issued Dec. 11, 2012 in International (PCT) Application No. PCT/JP2012/073300.

* cited by examiner

(A) PLACE RETAINER ON TRAY (B) IMMERSE FRAME IN AQUEOUS SOLUTION (C) FREEZE-DRYING (D) COMPLETED (E) TAKE OUT (WHEN IN USE)

COSMETIC TOOL, RETAINER OF COSMETIC MATERIAL AND METHOD OF MANUFACTURING COSMETIC TOOL

TECHNICAL FIELD

The present application discloses a cosmetic tool, a retainer of a cosmetic material and a method of manufacturing the cosmetic tool.

BACKGROUND ART

In recent years, a skin care has been practiced, which uses a cosmetic material sheet such as a mask or a pack (facial mask). The cosmetic material sheet involves using a nonwoven fabric or a woven fabric impregnated with skin care ingredients such as collagen, gelatin, hyaluronic acid, chitin, chitosan and amino acid or a mixture thereof (refer to, e.g., Patent document 1). The cosmetic material sheet using the nonwoven fabric or the woven fabric is impregnated with a lotion etc and thus patched to a skin surface.

Another type of cosmetic material sheet is proposed, in which only skin care ingredients such as synthetic polypeptide configuring a collagen-like structure undergo physical treatments, i.e., warming, cooling, freeze-drying, depressurization-drying, etc to form a sponge-like sheet, a gel-like sheet or a film-like sheet, and these sheets as utilized as the cosmetic material sheets (refer to Patent document 2). In this case, at first, a relatively large sheet is manufactured and is shape-cut or shape-punched corresponding to a dimensional shape of an applied region, and the shape-cut or shape-punched sheet is patched to the skin surface.

Moreover, still another type of cosmetic material sheet is proposed, which relaxes restraint against a behavior of a user during the patching of the cosmetic material sheet and facilitates treatment of the cosmetic material sheet, the structure being such that a sheet of the skin care ingredients is press-laminated on one-side surface of a base fabric composed of the water-repellent nonwoven or woven fabric having a shape and an area that enable an outer edge to be formed along the circumference of the sheet of the skin care ingredients (e.g., Patent document 3).

DOCUMENT OF PRIOR ART

Patent Document

[Patent document 1] Japanese Patent Application Laid-Open Publication No. 2005-263759
[Patent document 2] Japanese Patent Application Laid-Open Publication No. 2007-137875
[Patent document 3] Japanese Patent Application Laid-Open Publication No. 2010-163386

SUMMARY OF INVENTION

Problems to be Solved by the Invention

In the cosmetic material sheet configured by impregnating the skin care ingredients into the base fabric composed of the non-woven or woven fabric, the skin care ingredients remain on the base fabric after being used, and hence it follows that the skin care ingredients are inevitably discarded. Further, the cosmetic material sheet configured by freeze-drying the skin care ingredients such as collagen to form the sheet, is easy to cause cracks etc and therefore needs freeze-drying an aqueous solution of high-concentration skin care ingredients for ensuing strength to such an extent as to enable the sheet to be treated by fingers. When increasing the concentration of the skin care ingredients, however, the skin care ingredients remain as solid materials on the surface of the skin.

Under such circumstances, the present application aims at providing a retainer of a cosmetic material and a method of manufacturing a cosmetic tool, which are capable of easily treating the cosmetic material even when decreasing a concentration of skin care ingredients of the cosmetic material produced by freeze-drying.

Means for Solving the Problems

In order to solve the problems described above, according to the present invention, a cosmetic material is produced in a frame provided with a handle by freeze-drying an aqueous solution of skin care ingredients in a way that covers an aperture of another edge portion.

To be specific, according to the present invention, a cosmetic tool includes: a retainer to include an annular frame and a handle for holding the frame; and a cosmetic material to be produced by freeze-drying an aqueous solution of skin care ingredients and fixed in a way that covers an aperture of the frame.

The annular frame prevents hindrance against eliminating a water content of the aqueous solution when producing the cosmetic material by freeze-drying the aqueous solution of skin care ingredients and enables the cosmetic material to be fixed in a manner that covers the aperture of the frame. Moreover, a user does not directly touch the cosmetic material by holding the handle provided on the frame and can apply the cosmetic material to the skin by pinching the cosmetic tool.

The present cosmetic tool being thus configured, the user can pinch the cosmetic tool without directly touching the cosmetic material, and therefore almost no force is applied to the cosmetic material. When used, almost no force is applied to the cosmetic material, and hence the cracks etc are not caused even by decreasing the concentration of the skin care ingredients of the cosmetic material produced by the freeze-drying. Accordingly, the cosmetic material can be easily treated even by decreasing the concentration of the skin care ingredients.

It is to be noted that the frame may be partly formed with a notch and may also be configured to circle around annularly and continuously. The frame, if partly formed with the notch, is easy to get deformed, and hence the cosmetic material can be hermetically fitted to the skin. The frame, if configured to circle around annularly and continuously, is hard to get deformed and is therefore enabled to sufficiently retain the cosmetic material.

Further, the cosmetic material may contain at least any one of collagen, polypeptide, hyaluronic acid, pullulan and elastin. The cosmetic material contains these ingredients, thereby fostering a cosmetic effect on the skin of a region to which the cosmetic material is applied.

Moreover, the present invention can be grasped by way of a retainer of a cosmetic material. Namely, the present invention may be a retainer of a cosmetic material, including: an annular frame; and a handle for holding the frame, wherein the retainer retains a cosmetic material produced by freeze-drying an aqueous solution of skin care ingredients and fixed in a way that covers an aperture of the retainer.

Furthermore, the present invention can be grasped from an aspect of a method. For example, the present invention may be a method of manufacturing a cosmetic tool, including: immersing, by impregnating an aqueous solution of skin care ingredients in an annular frame of a retainer including the annular frame and a handle for holding the frame, the frame in the aqueous solution; and freeze-drying the aqueous solution in which the frame is immersed. The aqueous solution of skin care ingredients is impregnated into the retainer in away that immerses the annular frame in the solution and then freeze-dried, whereby the cosmetic tool described above can be produced efficiently with a comparatively small number of steps.

Further, the retainer may be stored in the storage portion to store the cosmetic tool, the aqueous solution may be impregnated into the frame of the retainer stored in the storage portion, the frame may be immersed in the aqueous solution, and the aqueous solution in which the frame is immersed may be freeze-dried. The cosmetic tool can be further efficiently produced by use of the storage portion to store the cosmetic tool on account of having no necessity for transferring the cosmetic tool into another container after being freeze-dried.

Effects of the Invention

According to the present invention, the cosmetic material can be easily treated even by decreasing the concentration of the skin care ingredients of the cosmetic material produced by the freeze-drying.

MODE FOR CARRYING OUT THE INVENTION

An embodiment of the present invention will hereinafter be described. The following embodiment is an exemplification, and a technical scope of the invention to be disclosed in the present application is not limited to the embodiment.

Figure 1:
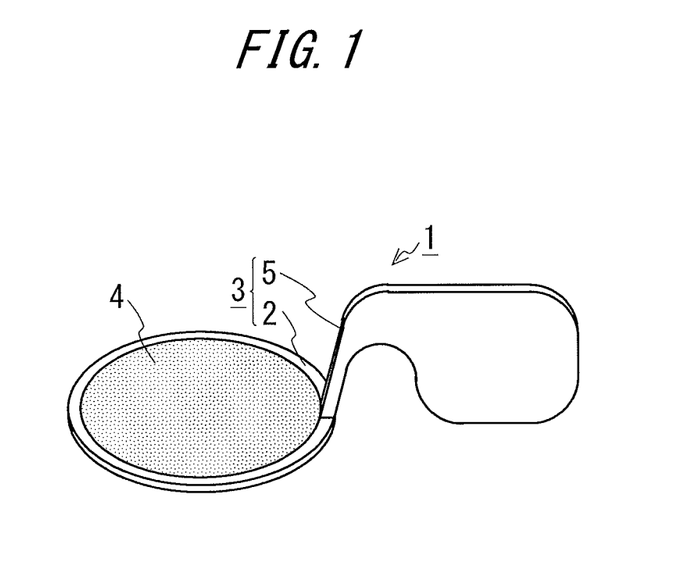
FIG. 1 is a view of an external appearance of a cosmetic tool.

FIG. 1 illustrates an external appearance of a cosmetic tool according to the embodiment. A cosmetic tool 1 includes, as depicted in FIG. 1, a retainer 3 having an annular frame 2 fitted with a handle 5, and a cosmetic material 4 retained over an interior area of the frame 2. The frame 2 takes a ring-like shape, and one handle 5 projects toward an outside of the frame 2. It is preferable that the frame 2 has a diameter and a thickness that are necessary for retaining the cosmetic material 4, in which the diameter is set to approximately 10 mm, and the thickness is set to approximately 1 mm. Further, it is preferable that the frame 2 is composed of a material that is easy for fingers to pinch and easy for the cosmetic material 4 to be fixed. This type of material can be exemplified such as polypropylene, PET (polyethylene terephthalate), silicon and nylon.

Figure 2:
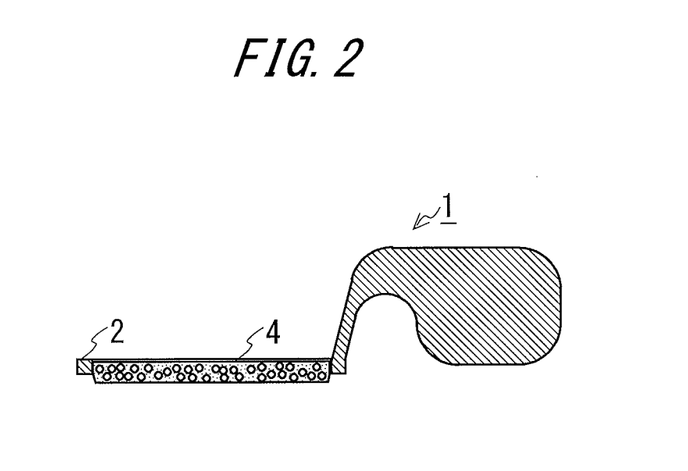
FIG. 2 is a view of a structure of the cosmetic tool.

FIG. 2 illustrates a structure of the cosmetic tool 1. The cosmetic tool 1 retains the sheet-shaped cosmetic material 4 in a way that covers an aperture of the frame 2. The cosmetic material 4 is produced by freeze-drying an aqueous solution of skin care ingredients. The skin care ingredients can be exemplified by collagen, synthetic polypeptide, hyaluronic acid, pullulan and elastin. The collagen, though the naturally existing collagen and the collagen produced by gene recombination are available, may also be synthetic collagen. The synthetic collagen can be exemplified by the synthetic polypeptide having an amino acid sequence expressed by the following formula, which configures a collagen-like structure. The synthetic collagen causes neither inflection of pathogens nor transmission of pathogenetic factors and therefore exhibits advantages of having high safety, high moisture retention and high stability and preventing an odor from being produced. The formula is given such as: (Pro-X-Gly)n In the formula given above, "X" represents "Pro" or "Hyp", "Pro" denotes a L-proline residue, "Hyp" denotes a L-hydroxyproline residue, "Gly" represents a glycine residue, and "n" is an integer of 1 through 100,000. Note that manufacture of the cosmetic material 4 may involve normally using additives such as a viscosity bodying agent and a diluting agent utilized for a cosmetic or medical use as the necessity may arise.

It is preferable that a concentration of the aqueous solution of skin care ingredients on the occasion of performing freeze-drying is such a concentration that effective ingredients effectively act on the skin, in which the concentration is set to, more preferably, e.g., 0.01%-1.0% by weight and, by far preferably, about 0.25% by weight. If the concentration of the aqueous solution of skin care ingredients is low, a structural strength of the cosmetic material 4 decreases, however, the cosmetic material 4 is fixed to the frame 2 by freeze-drying and thus solidifying the aqueous solution in a state where the frame 2 is immersed in the aqueous solution. Hence, even the cosmetic material 4 with the low concentration and the low structural strength, if retained over the frame 2, can be easily treated by pinching the frame 2 with the fingers. Note that the cosmetic material 4 with the high structural strength can be formed by increasing the concentration of the aqueous solution, however, in this case, it follows that the cosmetic material 4 remains as a solid material on the skin surface on the occasion of the use thereof by reason of the concentration being excessively high.

Figure 3:
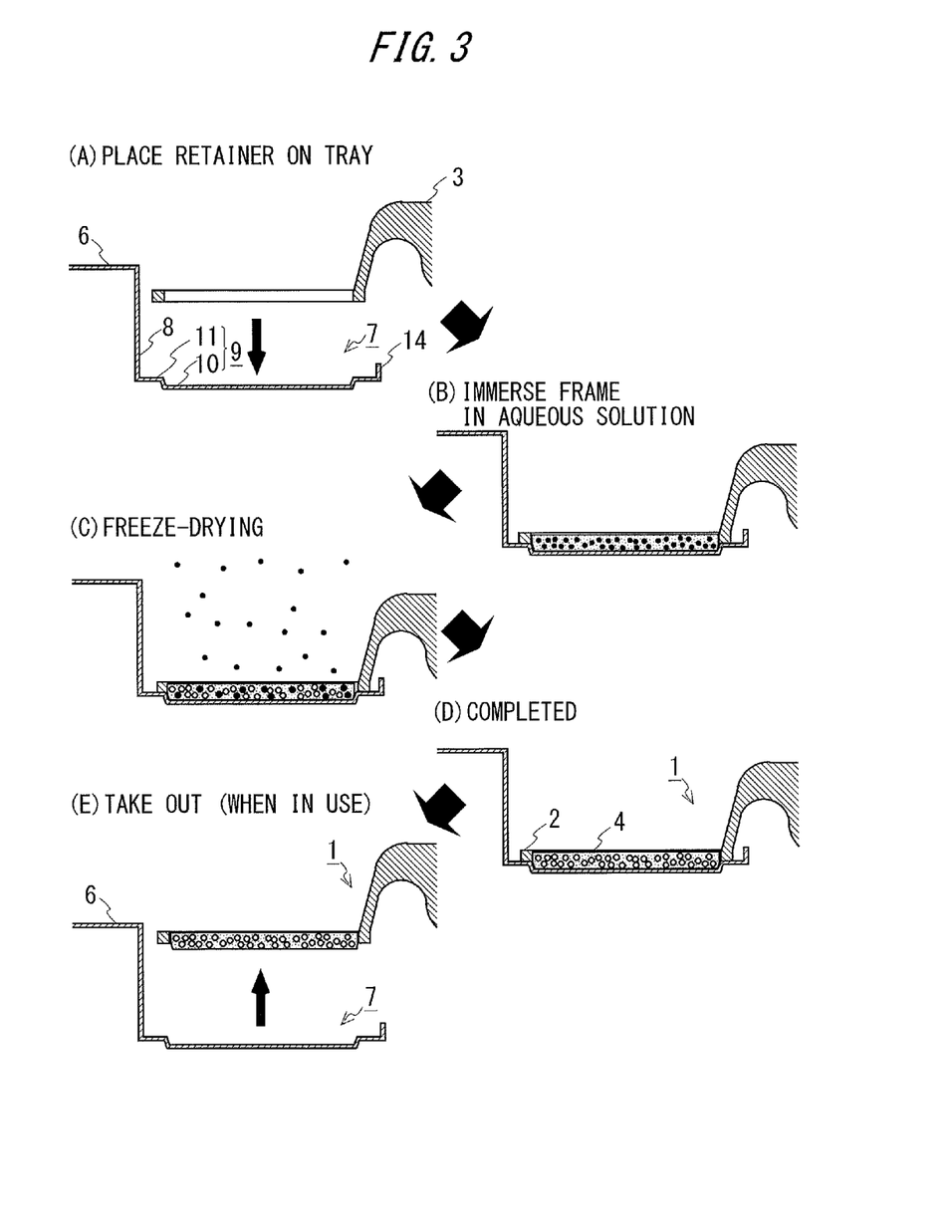
FIG. 3 is a view illustrating one example a manufacturing process of the cosmetic tool.

The cosmetic tool 1 can be manufactured, e.g., in the following processes. FIG. 3 illustrates one example of the manufacturing processes of the cosmetic tool 1.

On the occasion of manufacturing the cosmetic tool 1, the retainer 3 is placed on a tray 6 (FIG. 3(A)). The tray 6 is formed with a recessed storage portion 7 for storing the cosmetic tool 1, and the frame 2 is put into the storage portion 7. Herein, the storage portion 7 is a cylindrical storage portion along the annular frame 2 and includes a wall surface 8 for supporting a side portion of the cosmetic tool 1 and a bottom surface 9 for supporting a lower portion of the cosmetic tool 1. The bottom surface 9 of the storage portion 7 takes a circular shape, and a central portion thereof is lower by one step than an edge portion thereof. To be specific, in two surfaces configuring the bottom surface 9, a first bottom surface 10 forming the central portion of the bottom surface 9 is lower by one step than a second bottom surface 11 building up the edge portion of the bottom surface 9 and supporting an annular lower edge of the frame 2. Note that the bottom surface 9 is not necessarily configured by the two bottom surfaces having different heights as in the case of the first bottom surface 10 and the second bottom surface 11 but may be a flat surface with no step.

Next, the aqueous solution of skin care ingredients is impregnated into the interior of the frame 2, thus getting the lower portion of the frame 2 immersed in the aqueous solution (FIG. 3(B)). Then, the aqueous solution is freeze-dried (FIG. 3(C)). On the occasion of conducting the freeze-drying, in the state where the frame 2 is kept immersed in the aqueous solution, the aqueous solution is cooled together with the tray 6 and thus frozen. It is desirable that a temperature for freezing is sufficiently low, though corresponding to the ingredients in the aqueous solution.

After sufficiently freezing the aqueous solution in which the lower portion of the frame 2 is immersed, a space disposed of the tray 6 is vacuumized by reducing a pressure thereof. Then, the vacuum state is kept while supplying a necessary amount of heat for sublimating a water content of the aqueous solution to such an extent that the frozen aqueous solution is not dissolved. The frame 2 has the aperture, and hence the water content of the aqueous solution in which the lower portion of the frame 2 is immersed sublimates to pass through the interior of the frame 2. The water content of the aqueous solution is thereby sublimated, and eventually the aqueous solution gets freeze-dried, thus reaching completion of the cosmetic material 4 (FIG. 3(D)).

On the occasion of using the cosmetic tool 1, the cosmetic tool 1 is taken out of the tray 6 (FIG. 3(E)). The cosmetic material 4 is fixed to the frame 2 by conducting the freeze-drying and is therefore, when lifting up the frame 2 from the tray 6 by pinching the frame 2 with the fingers, exfoliated from the bottom surface 9 of the storage portion 7. When applying the cosmetic material 4 onto the skin wetted by spreading a lotion etc over the skin, the cosmetic material 4 gets dissolved on the skin. The cosmetic material 4 disappears when dissolved on the skin, and only the frame 2 fitted with the handle 5 is left in the cosmetic tool 1.

Figure 4:
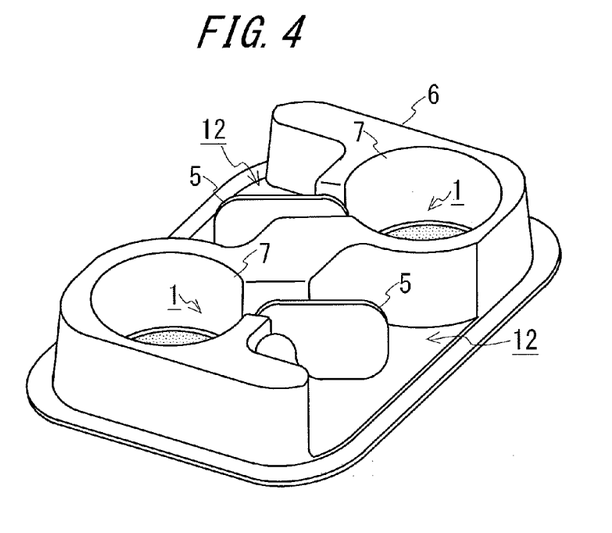
FIG. 4 is a view illustrating one example of a tray.
Figure 5:
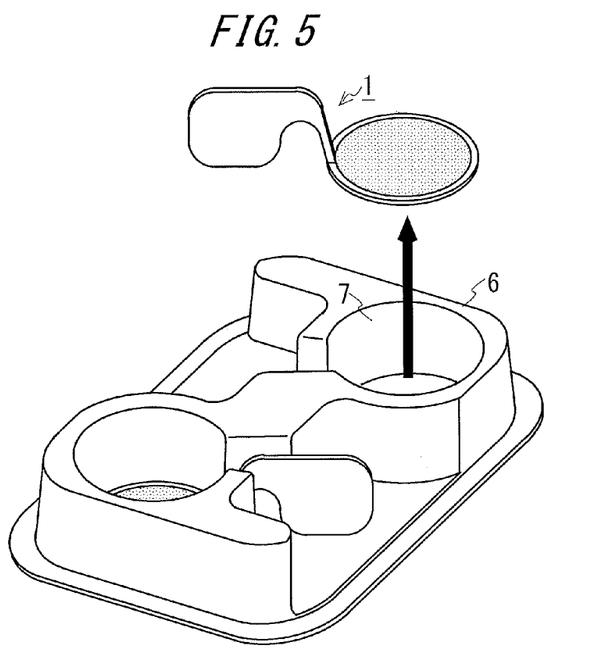
FIG. 5 is a view depicting how the cosmetic tool is taken out.

Note that the tray may be, as illustrated in FIG. 4, provided with the two storage portions 7, and the cosmetic tool 1 may be stored in each of the storage portions 7. In this case, the tray 6 may be provided with dents 12 by twos for every storage portion 7, in which the dent 12 is used for the handle 5 of the cosmetic tool 1 stored in the storage portion 7 to be pinched with the fingers. The dents 12 are provided adjacent to the respective storage portions 7, whereby the cosmetic tool 1 stored in the storage portion 7 can be easily pinched, and the cosmetic tool 1 is easily taken out of the storage portion 7 as depicted in FIG. 5. Note that the dent 12 needs configuring to prevent the aqueous solution impregnated in the interior of the frame 2 from flowing to the dent 12 out of the storage portion 7 in terms of convenience of the process of forming the cosmetic material 4 by the freeze-drying. Such being the case, a barrier 14 for blocking an outflow of the aqueous solution into the dent 12 is, as illustrated in FIG. 3, provided between the storage portion 7 and the dent 12. A root portion of the handle 5 of the cosmetic tool 1 is hollowed so as not to abut on this barrier 14 when the cosmetic tool 1 is stored in the storage portion 7.

Figure 6:
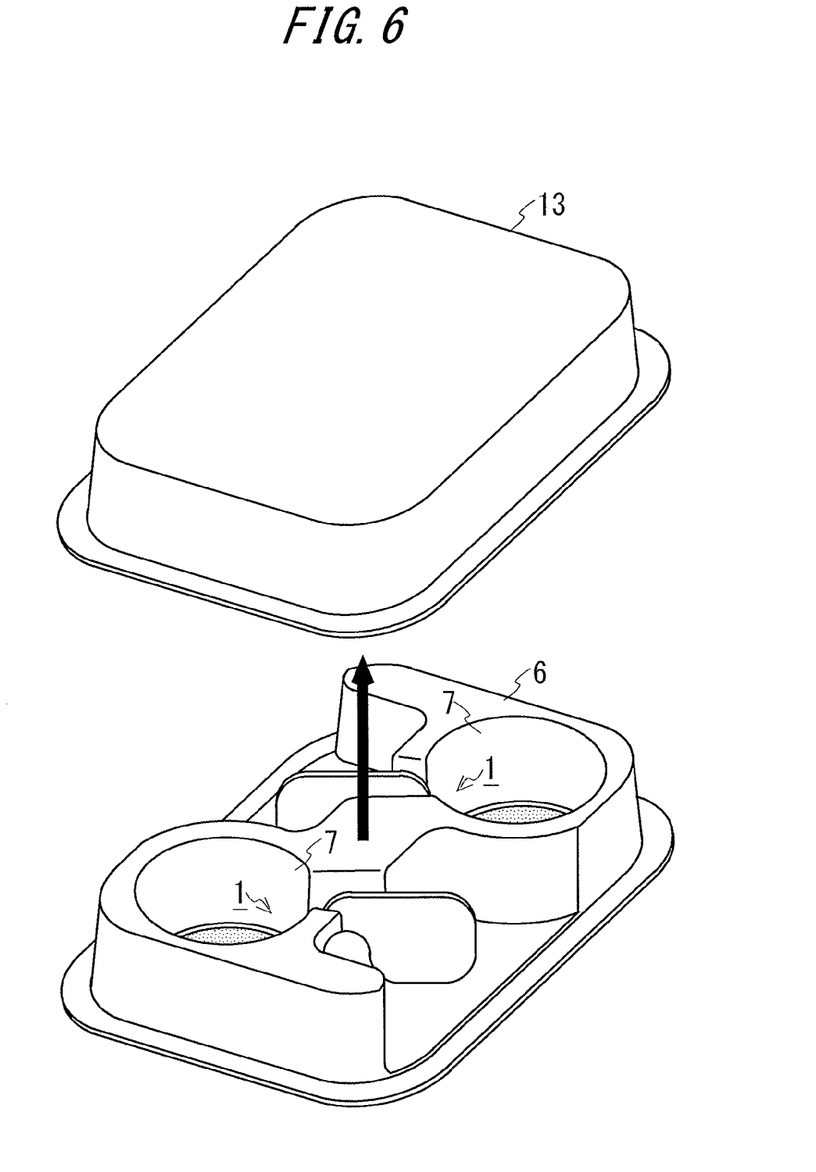
FIG. 6 is a view illustrating one example of a cap of the tray.

Further, the tray 6 may also be provided with, as illustrated in FIG. 6, an openable/closable cap 13. The openable/closable cap 13 is provided on the tray 6, whereby any one of the cosmetic tools 1 stored in the respective storage portions 7 is taken out for the use, while another cosmetic tool 1 can be kept in an as-stored state in the storage portion 7 being hermetically closed.

Figure 7:
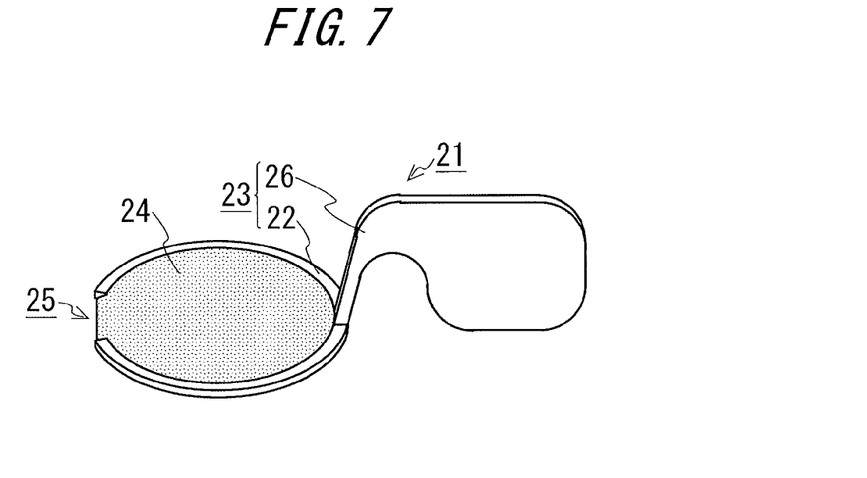
FIG. 7 is a view of a modified example of the cosmetic tool.

FIG. 7 illustrates an external appearance of the cosmetic tool according to a modified example. A cosmetic tool 21 according to the modified example includes, as illustrated in FIG. 7, a notch 25 formed in a part of the annular frame 2, thus making the frame 2 discontinuous. A retainer 23 is structured to fit a handle 26 to a frame 22 being partly formed with the notch 25. Then, a cosmetic material 24 is retained in the interior of the frame 22 including the notch 25. Conditions about a dimension and a material of the retainer 23 are the same as those of the retainer 3. With respect to the frame 22 also that includes the notch 25 described above, in the same way as the continuous annular frame 2, after the frame 22 has been immersed in the aqueous solution of skin care ingredients, the freeze-drying process is carried out, thereby forming the cosmetic material 24. In the case of the frame 22 including the notch 25, the frame 22 gets deformed easier than the continuous annular frame 2, and hence the cosmetic material 24 can be tightly fitted to the skin.

It is to be noted that an inner peripheral portion, for retaining the cosmetic material, of the frame may be provided with pawls for preventing the cosmetic material from being released and may also undergo a ruggedness forming work.

[Working Example]

<Manufacture of Cosmetic Tool>

The frame is stored in the storage portion, and a tray impregnated with an aqueous solution of the synthetic collagen that is 0.25% by weight (a 0.5% aqueous solution of "PURECOLLA (registered trademark)", a product name of JNC Corp., is diluted with pure water) is put into a freeze-drying machine (a product name; EYELA FDU-1100 (made by Tokyo Rikakikai Co., Ltd.), a product name of an angular dry chamber: EYELA DRC-1000 (made by Tokyo Rikakikai Co., Ltd.), a vacuum pump: ULVAC-200 (made by ULVAC Kiko, Inc.)) and is frozen by its being cooled for 10 hours till reaching −50° C. Thereafter, the tray is freeze-dried at −50° C. for 10 hours by operating the vacuum pump and is taken out of the freeze-drying machine afterward by increasing the temperature back to 25° C. As a result, it is confirmed that the cosmetic material, which is approximately 1 mm in apparent thickness, has been produced.

<Evaluation of Usability>

The lotion is spread over the skin beneath eyes, and the cosmetic material of the cosmetic tool manufactured by the method described above is applied thereto. When the cosmetic material is applied thereto, the applied cosmetic material is dissolved by the lotion spreading over the skin. In the case of having no frame fitted with the handle, the cosmetic material is dissolved on the finger's surface or is damaged by finger's force when pinching the cosmetic material and is therefore hard to be sufficiently applied to a desired region. As in the present application, however, the use of the frame fitted with the handle enables the cosmetic material to be dissolved and spread over the desired region.

DESCRIPTION OF THE REFERENCE NUMERALS AND SYMBOLS 1, 21 . . . cosmetic tool
2, 22 . . . frame
3, 23 . . . retainer
4, 24 . . . cosmetic material
5, 26 . . . handle
6 . . . tray
7 . . . storage portion
8 . . . wall surface
9 . . . bottom surface
10 . . . first bottom surface
11 . . . second bottom surface
12 . . . dent 13 . . . cap
14 . . . barrier
25 . . . notch

The invention claimed is:

1. A method of manufacturing a cosmetic tool, comprising:
proving a retainer having: a frame of a thickness of approximately 1 mm that forms an aperture; and a handle for holding the frame;
immersing the frame in aqueous solution of skin care ingredients so as to impregnate the aqueous solution in the frame; and
freeze-drying the aqueous solution while the frame is immersed therein such that the aqueous solution forms a cosmetic material that closes the aperture of the frame.

2. The method of claim 1, wherein the cosmetic material contains at least any one collagen, polypeptide, hyaluronic acid, pullulan and elastin.

3. The method of claim 1, wherein the frame is formed as an annular frame.

4. The method of claim 1, wherein the frame is formed with a notch.

5. The method of manufacturing the cosmetic tool, comprising:
providing a retainer having: a frame of a thickness of approximately 1 mm that forms an aperture; and a handle for holding the frame;
storing the retainer in a storage portion;
immersing the frame in an aqueous solution of skin care ingredients so as to impregnate the aqueous solution in the frame stored in the storage portion; and
freeze-drying the aqueous solution while the frame is immersed therein such that the aqueous solution forms a cosmetic material that closes the aperture of the frame.

6. The method of claim 5, wherein the cosmetic material contains at least any one collagen, polypeptide, hyaluronic acid, pullulan and elastin.

7. The method of claim 5, wherein the frame is formed as an annular frame.

8. The method of claim 5, wherein the frame is formed with a notch.

* * * * *

UNITED STATES PATENT AND TRADEMARK OFFICE
CERTIFICATE OF CORRECTION

PATENT NO.         : 9,648,938 B2                                    Page 1 of 1
APPLICATION NO.    : 14/345784
DATED              : May 16, 2017
INVENTOR(S)        : Takafumi Takebayashi It is certified that error appears in the above-identified patent and that said Letters Patent is hereby corrected as shown below:

In the Claims

Column 7, Claim 2, Line 18, "contains at least any one collagen, polypeptide, hyaluronic" should read -- contains at least any one of collagen, polypeptide, hyaluronic --.

Column 8, Claim 5, Line 1, "The method of manufacturing the cosmetic tool, com-" should read -- A method of manufacturing a cosmetic tool, com- --.

Column 8, Claim 6, Line 15, "contains at least any one collagen, polypeptide, hyaluronic" should read -- contains at least any one of collagen, polypeptide, hyaluronic --.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*